United States Patent [19]
Wan et al.

[11] Patent Number: 5,342,374
[45] Date of Patent: Aug. 30, 1994

[54] SUTURE GUIDING DEVICE AND METHOD OF USE

[76] Inventors: Shaw P. Wan, 603 Lariat La., Rolla, Mo. 65401; Rosendo Martinez, 790 Prigge Rd., St. Louis, Mo. 63138

[21] Appl. No.: 992,494

[22] Filed: Dec. 17, 1992

[51] Int. Cl.⁵ .............................................. A61B 17/04
[52] U.S. Cl. ..................................................... 606/148
[58] Field of Search ............... 606/139, 144, 147, 145, 606/148, 150

[56] References Cited

U.S. PATENT DOCUMENTS

| | | | |
|---|---|---|---|
| 659,422 | 10/1900 | Shidler . | |
| 2,897,820 | 8/1959 | Tauber | 606/148 |
| 3,877,434 | 4/1975 | Ferguson et al. | 606/148 |
| 4,597,390 | 7/1986 | Mulhollan et al. | 606/148 |
| 4,911,164 | 3/1990 | Roth | 606/148 |
| 5,053,043 | 10/1991 | Gottesman et al. | 606/148 |

OTHER PUBLICATIONS

R. Taylor, A. M., M.D., Genito-Urinary and Venereal Diseases and Syphilis, p. 186 (Lea Bros. & Co. 3d ed. 1904).

M. Campbell, M. S., M.D., F.A.C.S., Urology vol. Two, pp. 940–941 (W. B. Saunders Company 1954).
Urological Surgical Instruments, catalog from V. Muller, p. C5, 1988.

*Primary Examiner*—Tamara L. Graysay
*Attorney, Agent, or Firm*—Senniger, Powers, Leavitt & Roedel

[57] ABSTRACT

A suture guiding device comprising a tubular shaft having opposite ends which are distal and proximal relative to a person holding the device for use in a suturing procedure, the distal end of the shaft being adapted to be inserted into a patient during the procedure. A suture guide is mounted at the distal end of the shaft for rotation relative to the shaft about an axis extending endwise with respect to the shaft. The guide has a guide surface for guiding a suture needle. A hand-operable control device is mounted on the shaft generally adjacent its proximal end. The guide and the control device are connected whereby hand-operation of the control device effects rotation of the guide to selectively adjust the suture-guiding position of the guide surface.

22 Claims, 5 Drawing Sheets

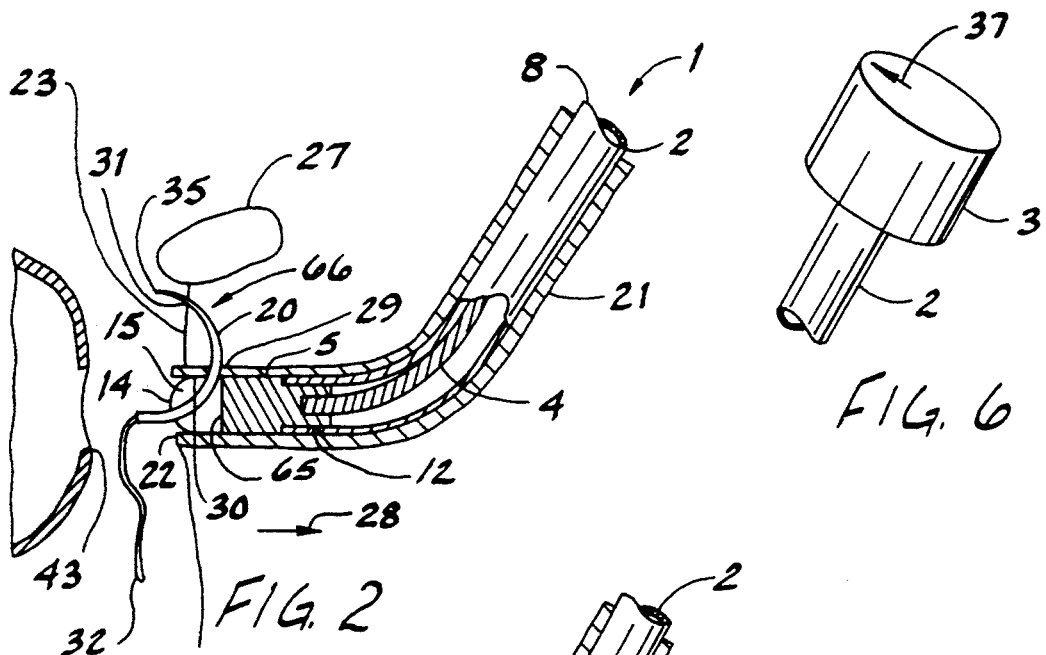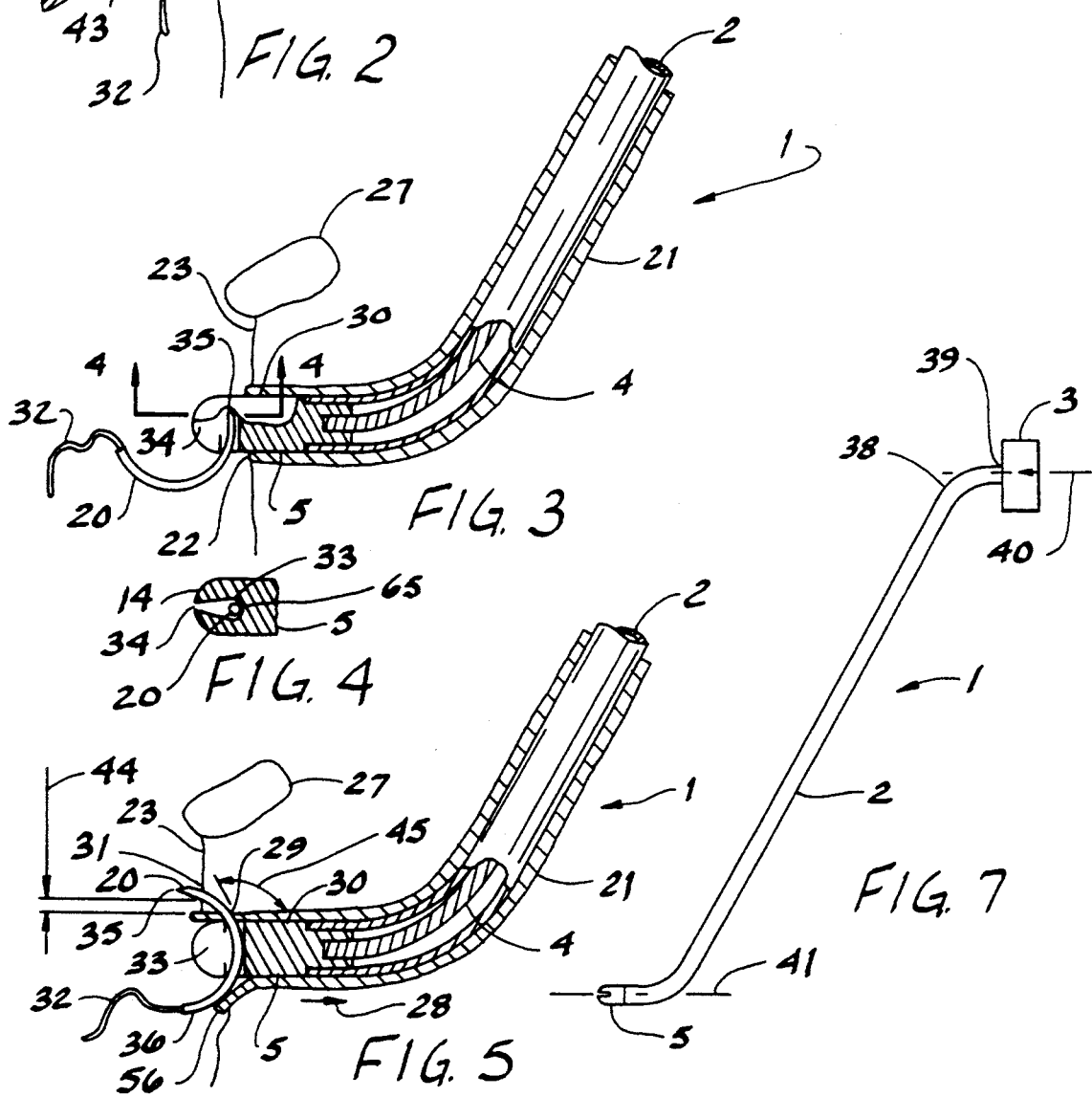

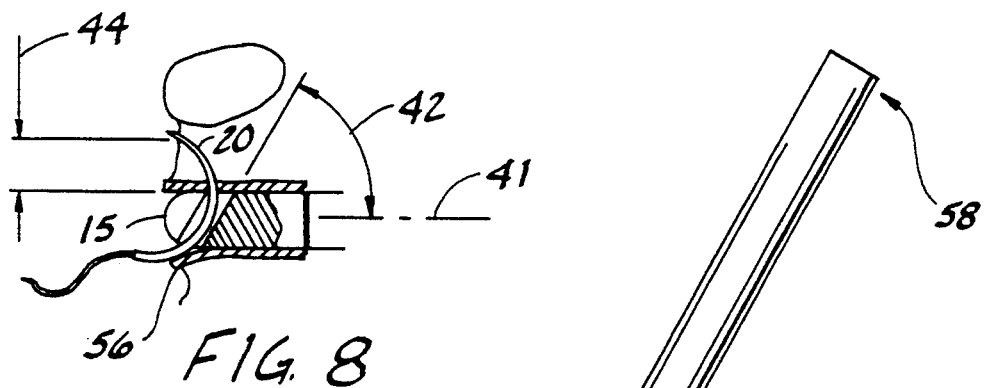
FIG. 8
FIG. 10B
FIG. 10A
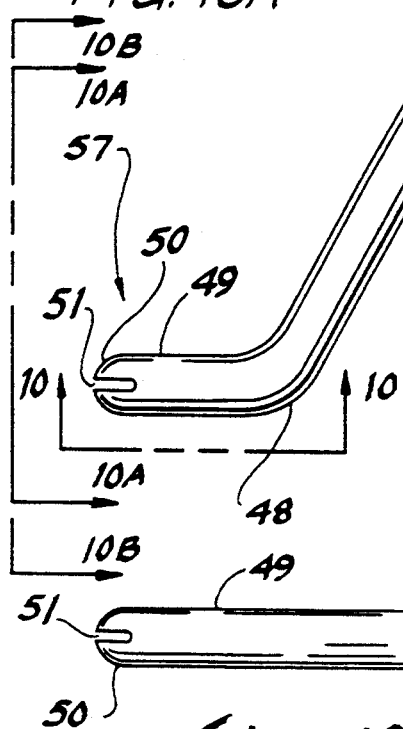
FIG. 9
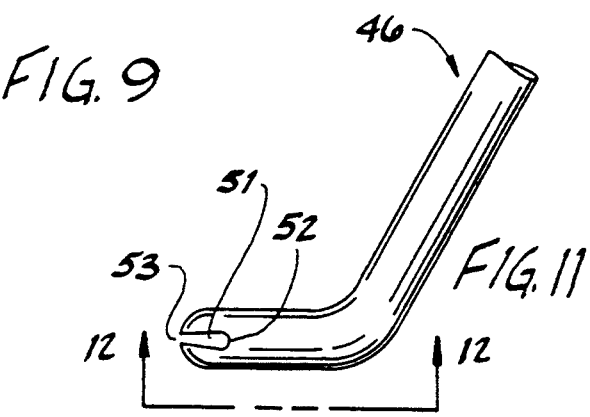
FIG. 11
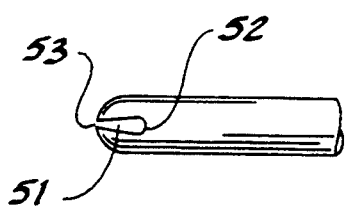
FIG. 10
FIG. 12

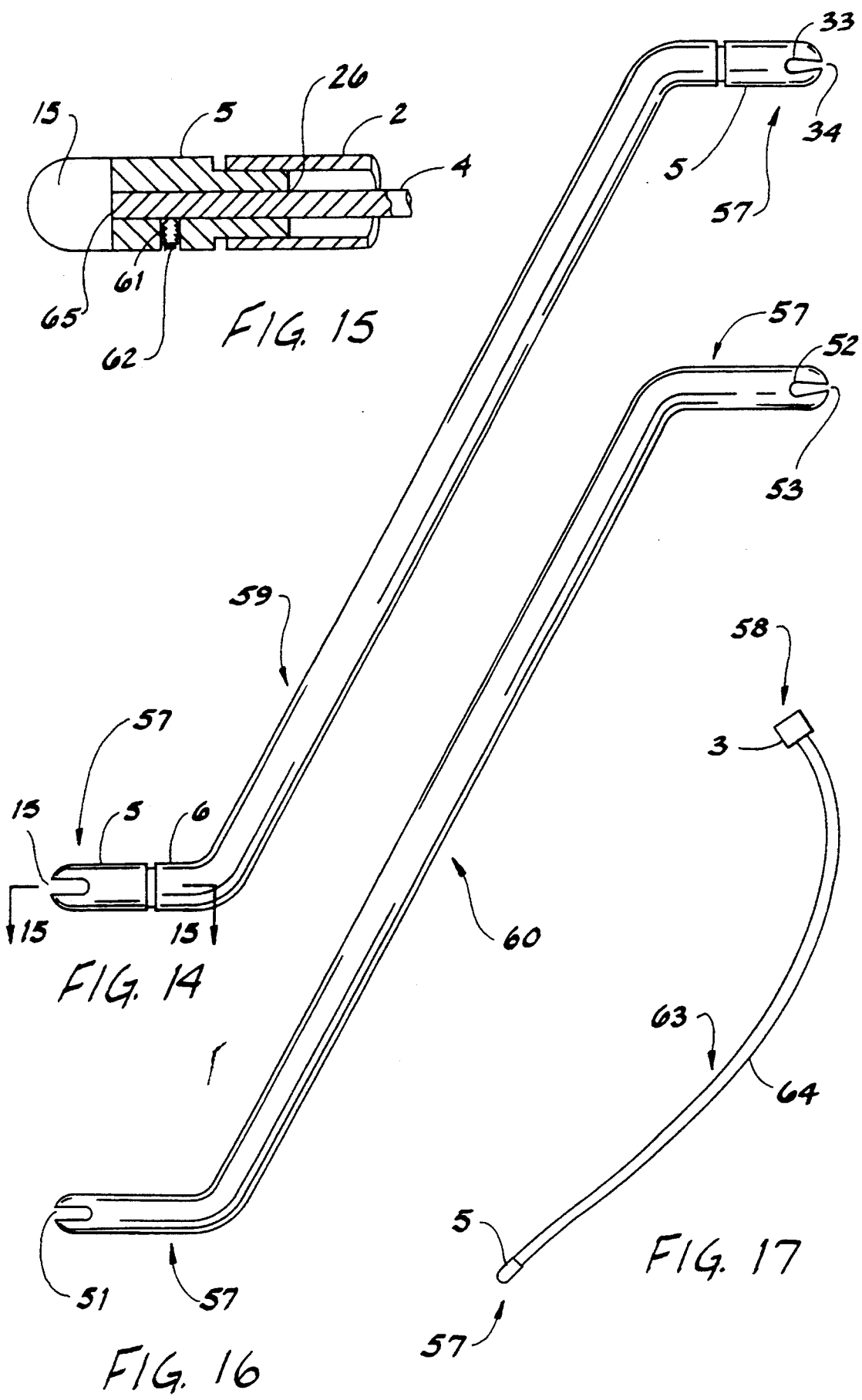

SUTURE GUIDING DEVICE AND METHOD OF USE

BACKGROUND OF INVENTION

The present invention relates to a suture guiding device, specifically, but not limited to, the type used during a radical prostatectomy procedure or anastomosing two tubular structures.

At the present time, there are few suture guide techniques. For many years surgeons have been using a Foley catheter, perineal pressure, or traction suture to facilitate the placement of the suture 10 during anastomosis of the urethra to the bladder neck. The retraction of the short urethral stump has made this a technical challenge.

More recently suture guides have been developed to improve the anastomosis.

For example, the device described in U.S. Pat. No. 2,897,820, (Robert Tauber) is used to ligate tissue structures by guiding the curved needle after it has passed through body tissue or anastomosing large diameter tubular structures, but it is not suitable to anastomose the urethral stump because of the physical constraints of the male body. His device can place sutures only in one location. This makes it impossible to place subsequent sutures around the urethral stump.

U.S. Pat. No. 4,911,164 (Robert A. Roth) describes a suture guide that is a modification of the standard urethral sound as Dr. Robert W. Taylor shows in his 1904 edition of *Practical Treatise On Genito-Urinary Venereal Diseases And Syphilis* book. Roth's device includes at least one groove which extends from the tip of the sound into the curved portion of the sound. However, if only one deep groove is provided, a suture can be placed only in one position with respect to the stump because the suture guide cannot be rotated inside the male urethra. Thus, if more than one suture location is required, it is necessary to withdraw the sound from the patient and replace it with another sound containing a groove in a different location which is then reinserted into the patient. It is necessary to repeat this procedure as many times as the number of sutures required. Obviously, this is time-consuming and technically cumbersome. As it can be seen in Roth's illustration, if more than one groove is placed around the sound, this configuration will require very shallow grooves. These shallow grooves will guide the needle at an angle that will cause it to embed deep into the surrounding tissue as it advances through the urethral stump. The retrieval of the needle then becomes very difficult. Roth attempted to solve the problem of urethral stump retraction by adding expanding elements to push the urethral stump outward. However, this addition to the guide risks potential damage to the urethral stump by tearing the urethral tissue. Other patents, such as U.S. Pat. No. 5,053,043 (James E. Gottesman), show suture guiding devices which incorporate an interchangeable, freely rotatable tip on a urethral sound. Mr Gottesman's invention does not have a slit in the tip of his suture guide. Furthermore, rotation of the tip cannot be controlled externally but instead requires manipulation of the tip inside the body cavity at the suture end. Since the tip is freely rotatable, it is difficult to stabilize during suture placement.

SUMMARY OF THE INVENTION

Among the several objects of this invention may be noted the provision of an improved suture guiding device; the provision of such a device which is particularly useful in a radical prostatectomy procedure or in anastomosing two tubular structures; the provision of such a suture guiding device which includes a suture guide which may be conveniently rotated during the procedure to selectively adjust the suture-guiding position of the guide; the provision of such a device which is capable of pulling suture thread to a desired point of needle penetration inside a tubular structure to be sutured, such as the urethral stump; the provision of such a suture guiding device which may incorporate multiple suture guides of different configuration for appropriate selection by a surgeon according to need; the provision of such a suture guiding device which causes a curved suture needle to move in an exit direction as soon as the needle penetrates the wall of a tubular structure being sutured, thereby avoiding the needle taking too large a "bite" into surrounding tissue, and further avoiding entrapment of the needle in surrounding tissue or bone; and the provision of a method of using such suture guiding device.

Briefly, a suture guiding device of the present invention comprises a tubular shaft having opposite ends which are distal and proximal relative to a person holding the device for use in a suturing procedure, the distal end of the shaft being adapted to be inserted into a patient during said procedure. A suture guide is mounted at the distal end of the shaft for rotation relative to the shaft about an axis extending endwise with respect to the shaft. The guide has a guide surface for guiding a suture needle. A hand-operable control device is mounted on the shaft generally adjacent its proximal end. The device also includes means interconnecting the guide and the control device whereby hand-operation of the control device is adapted to effect rotation of the guide to selectively adjust the suture-guiding position of said guide surface.

In another aspect of this invention, the suture guiding device comprises a shaft having opposite ends which are distal and proximal relative to a person holding the device for use in a suturing procedure. The distal end of the shaft forms a guide and is adapted to be inserted into a patient during the procedure. At least one end slit in the guide extends endwise proximally inwardly from the distal end of the shaft and laterally across the shaft from one side of the shaft to an opposite side of the shaft. The end slit has a proximal portion adjacent the bottom of the slit forming a needle passage through the guide from one side of the guide to said opposite side of the guide, and a distal portion extending distally outwardly from the passage along the length of the passage. The needle passage has a guide surface configured for guiding a suture needle pulling a suture thread as it passes through said passage. The suture thread is adapted to be removed from the guide after the suture needle has passed though the passage by moving the thread from the proximal portion of the slit distally outwardly through the distal portion of the slit for exit from the slit.

The method of this invention involves performing a suturing procedure on an anatomical element utilizing a suture guiding device of the type comprising a shaft having opposite ends which are distal and proximal relative to a person holding the device for use in said suturing procedure, a guide at the distal end of the shaft, and at least one end slit in the guide extending proximally inwardly from a distal end of the guide and laterally across the guide from one side of the guide to an opposite side of the guide, the slit having a proximate portion adjacent the bottom of the slit forming a needle passage, and a distal portion extending distally outwardly from the needle passage along the length of the passage. The passage has a guide surface configured for guiding a suture needle pulling a suture thread. The method comprises the steps of:

inserting the shaft into a patient to a preliminary position in which the guide projects distally beyond said element to be sutured;

placing at least the tip of a suture needle in the end slit in the guide so that the tip is unexposed to said element;

retracting the shaft and the guide with at least the tip of the needle therein to a suturing position in which the needle is positioned for suturing said element;

passing the suture needle through the needle passage in the guide with the needle in contact with the guide surface so that the needle is guided into and through the element to be sutured for a distance sufficient to pull a leading length of suture thread through the element while leaving a trailing length of suture thread in the guide; and removing the trailing length of thread from the guide by passing it distally outwardly through the outwardly opening distal portion of the slit.

BRIEF DESCRIPTION OF THE DRAWINGS

In the drawings:

FIG. 2 is a sectional view of a portion of the suture guiding device of FIG. 1 showing the device as used in a suturing procedure.

FIG. 3 is a sectional view similar to FIG. 2 showing an alternative embodiment of the device incorporating a suture guide with needle pulling means.

FIG. 4 is a sectional view of the suture guide shown in FIG. 3.

FIG. 5 is a view similar to FIG. 3 illustrating a continuation of the procedure FIG. 3.

FIG. 6 is an isometric view of a portion of a suture guiding device of FIG. 1 showing an alternative design.

FIG. 7 is a side view of an alternative embodiment of the device in FIG. 1.

FIG. 8 is a sectional view of an alternative embodiment of the device shown FIGS. 3 and 5.

FIG. 9 is a side view of a one piece suture guiding device of this invention.

FIG. 10 an side view of the device in FIG. 9.

FIG. 10A is an end view of the device in FIG. 9.

FIG. 10B is an end view similar to FIG. 10A but showing an alternative slit design.

FIG. 11 is a side view of an alternative embodiment of the device in FIG. 9.

FIG. 12 is a side view of the device in FIG. 11.

FIG. 14 is a reversible, externally controlled, rotational suture guiding device with slit and needle pulling means.

FIG. 15 is an enlarger sectional view of a portion of the device in FIG. 14.

FIG. 16 is a one-piece reversible suture guiding device with slit and needle pulling means.

FIG. 17 is a flexible, externally controlled, rotational suture guiding device.

DETAILED DESCRIPTION OF THE INVENTION

Figure 1:
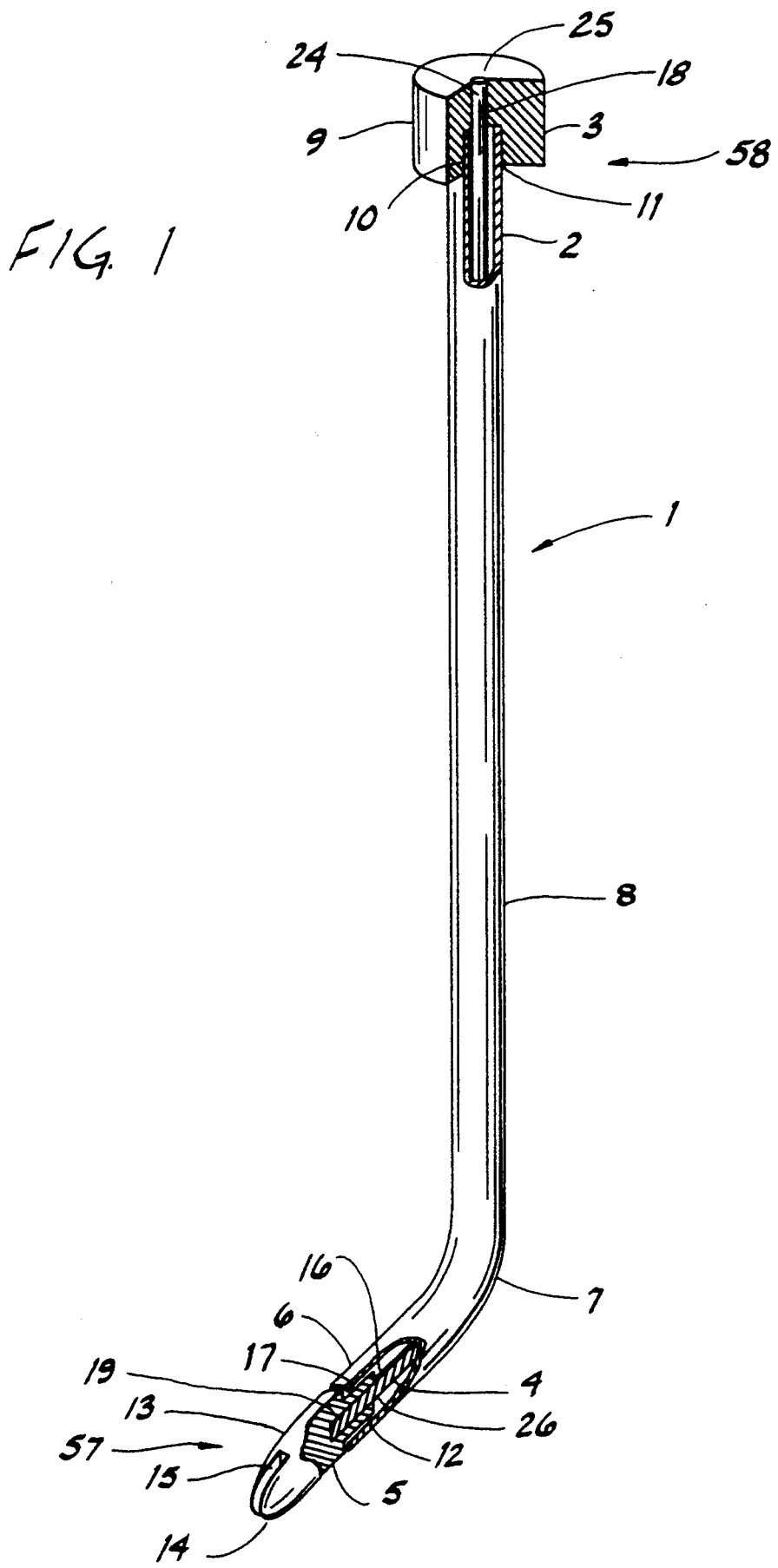
FIG. 1 is an isometric view of an externally controlled, rotational suture guiding device of the present invention.

Referring now in more detail to the drawings which illustrate practical embodiments of the present invention, FIG. 1 shows an externally controlled, rotational suture guiding device, generally designated 1.

As shown in FIG. 1, the externally controlled, rotational suture guiding device 1 comprises a tubular shaft 2 having opposite ends which are distal 57 and proximal 58 relative to a person holding the device for use in a suturing procedure, the distal end 57 of the shaft being adapted to be inserted into a patient during the procedure. The device 1 further comprises a suture guide 5 mounted at the distal end 57 of the tubular shaft 2 for rotation relative to the tubular shaft 2 about an axis extending endwise with respect to the tubular shaft 2, a control knob 3 at the proximal end 58 and means comprising a flexible shaft 4 interconnecting the suture guide 5 and the control knob 3.

The tubular shaft 2 has a short, straight tubular distal section 6, followed by a curved tubular section 7, followed by a long, straight tubular section 8. When the suture guiding device 1 is in use, the tubular shaft 2 must be capable of being manually grasped at the long, straight tubular section 8, and kept in control by the surgeon while inserted into the urethral meatus and guided all the way through the urethra 21 to eventually protrude out of the urethral stump 22 in the same manner as a standard urethral sound is used.

The control knob 3 consists of a member 9 with a counterbore 10 and a small diameter hole 25. The counterbore 10 has to be capable of spinning around end 11 of tubular shaft 2. The counterbore 10 has to be deep enough to support and stabilize control knob 3 on end 11 of tubular shaft 2. The small hole 25 is the portion of the control knob 3 that accepts and holds flexible shaft 4.

Suture guide 5 is an elongated member extending axially with respect to distal end portion 6 of the tubular shaft. The guide 5 has a smaller diameter proximal end portion 12 with a small hole 26 extending axially of the guide, a larger diameter middle portion 13, and a blunt distal end portion 14. A generally channel shaped slit 15 is formed in the blunt end portion 14 and extends into the larger diameter middle portion 13. The slit 15 is wide enough to allow passage of a curved needle 20 through the blunt end portion 14 and into the middle shaft portion 13. As shown in FIG. 1 and 2, the slit 15 has an open mouth, generally parallel side walls and a bottom surface or floor 65 which extends generally perpendicular to the longitudinal axis of the guide 5.

End 24 of flexible shaft 4 is attached at 18 firmly inside hole 25 of control knob 3. The shaft 4 extends through the tubular shaft 2 and is attached at 19 firmly inside hole 26 of suture guide 5.

Small diameter proximal end portion 12 of suture guide 5 is capable of spinning inside end 17 of tubular shaft 2. The proximal end portion 12 of suture guide 5 must be long enough to support and stabilize itself inside end 17 of tubular shaft 2.

As it can be seen, when control knob 3 is manually rotated, the flexible shaft 4 is capable of transmitting the rotation to the suture guide 5. This rotation allows the slit 15 in the guide to be oriented at any location around the urethral stump 22 during a radical prostatectomy procedure or tubular anastomosis.

As shown in FIG. 2, when a surgeon is uniting the bladder neck 43 to the urethral stump 22, a curved needle 20 pulling a suture thread 32 has to be inserted through the urethral stump 22 and its surrounding tissue 23, without going through the pubic bone 27.

With our invention, the externally controlled, rotational suture guiding device 1 is inserted inside the urethra 21 in the same way as a standard urethral sound by inserting the blunt distal end portion 14 of the guide into the urethral meatus until the blunt end portion 14 protrudes out of the urethral stump 22. After the suture guiding device 1 is in place, the long straight tubular portion 8 of tubular shaft 2 is housed inside the penis and the suture guide 5 extends out through the urethral stump 22.

When the blunt distal end portion 14 is observed, control knob 3 is manually rotated by the surgeon. The rotation of control knob 3 will cause flexible shaft 4 to rotate, which will cause the small diameter proximal end portion 12 of the suture guide 5 to rotate inside the distal end 17 of tubular shaft 2.

The surgeon will be capable of controlling the rotation of the suture guide 5 until the slit 15 in the blunt end portion 14 is at the desired position of suture insertion. After the desired orientation of slit 15 is obtained, curved needle 20 is inserted inside the slit 15.

As can be observed, curved needle 20 is capable of being positioned in two different orientations 180 degrees apart. Therefore, two sutures can be placed with a single rotation of the suture guide 5.

After the curved needle 20 is placed inside slit 15, the suture guiding device 1 can be pulled back slightly 28 until the surgeon is capable of finding the desired location of needle entry 29 into the urethral internal wall 30. The needle 20 is then pushed through the slit 15 with the needle 20 in contact with the bottom (guide) surface 65 of the slit 15 to guide the needle 20 so that it enters nearly perpendicular to the urethral internal wall 30. After nearly perpendicular entry, the curved needle 20 will then head in an exit direction the moment the curved needle 20 starts to penetrate the urethral internal wall 30. It is therefore possible to drive the curved needle 20 through without touching the pubic bone 27 or losing the needle 20 inside the surrounding tissue 23. After the needle 20 exits tissue 23 at 31, the surgeon will be capable of grabbing the needle tip 35 outside the urethral stump 22 and the surrounding tissue 23, leaving the suture thread 32 inside the urethral stump 22 and the surrounding tissue 23.

After a suture 66 has been placed inside the urethral stump 22 and the surrounding tissue 23 at a superior or other chosen position, an additional suture can be placed in the urethral stump 22 180 degrees away from the first suture in the same way the first suture was placed. Traction applied to both ends of the suture thread 32 will disengage the suture thread from the suture guide (the thread moves from the proximal portion of the slit 15 distally outwardly through the distal portion of the slit and thus exit the slit). It is now possible to turn control knob 3 to rotate suture guide 5 to the next desirable position. The suture guiding device 1 is next pushed back into the urethra 21. The slit 15 will protrude once again through the urethral stump 22. At this time, the previously placed sutures 66, will be between the urethral internal wall 30 and the suture guide 5 will be out of the way of the slit 15. Now the surgeon will be able to place additional sutures.

FIG. 3 and FIG. 4 illustrate an alternative embodiment of the suture guiding device in which the slit 15 is modified. The slit 15 in portion 13 of the suture guide 5 has a proximal portion with a wide separation or width 33 large enough to allow passage of curved needle 20, and a distal portion with a narrow separation or width 34 toward the blunt end portion 14 of the guide (i.e.,adjacent, the open mouth of the channel-shaped slit), allowing passage of suture thread 32 but not passage of the larger diameter curved needle 20. In this embodiment, the configuration of the slit 15 also functions as a needle pulling means, as will be described.

As shown in FIG. 3, the suture guiding device 1 with needle pulling means is inserted through the urethra 21 until the wide separation 33 can be observed as it protrudes out of the urethral stump 22. The curved needle 20 is then inserted into but not through the wide separation 33 of slit 15 to a position in which the needle tip 35 is lodged inside the narrow separation 34. As shown in FIG. 5, the suture guide 5 is then pulled back slightly into the urethra 21 (as indicated by the directional arrow 28 in FIG. 2), thereby pulling the needle 20 into the urethra 21. This action causes the curved portion 36 of the needle 20 to displace the urethral stump and the surrounding tissue 56. Retraction of the suture guiding device 1 is continued until the desired location of needle entry 29 is determined by the surgeon. The surgeon then dislodges the tip 35 of the needle 20 from the narrow separation 34 and pushes the needle through passage 33 with the needle in contact with the bottom guide surface 65 to guide the needle 20 into the urethral internal wall 30, proceeding through the surrounding tissue 23, until the curved needle 20 exits at 31. The surgeon can then grasp and pull the needle tip 35 to complete the suturing. Notice that this time the curved needle 20 does not enter perpendicularly, but at an obtuse angle 45 relative to the urethral internal wall 30, allowing the curved needle 20 to take a smaller bite 44 out of the surrounding tissue. It is important to notice that this embodiment prevents the curved needle 20 from scraping the urethral internal wall 30 when the curved needle 20 is inserted into the urethra.

FIG. 6 illustrates another embodiment of the present invention. As shown in FIG. 6, indicia 37 (e. g., an arrow) is provide on the control knob 3 to indicate the direction of the slit 15 in the guide 5. This enables the surgeon to observe the direction of the slit 15 even when the suture guide 5 is obscured by the urethra 21.

FIG. 7 depicts another embodiment of the present invention. As shown, the tubular shaft 2 includes another curved portion 38 followed by a short, straight portion 39 at the proximal end 11 of tubular shaft 2 next to control knob 3. This configuration places the axis 40 of the control knob 3 substantially parallel to the axis 41 of the suture guide 5 and allows easier manipulation of the instrument under certain circumstances.

FIG. 8 presents another embodiment of this invention. As shown in FIG. 8, the wide separation 33 and bottom guide surface 65 of the slit 15 extend obliquely in relation to the rotational axis 41 of the suture guide 5 at an acute angle 42. This slant enables the surgeon to better control the amount of bite 44 when he inserts needle 20, compare to a perpendicular angle 42.

With a perpendicular angle 42, the amount of bite 44 is determined by the surgeon, depending on the amount of protrusion of blunt end portion 14 out of the urethral stump 22. With a slant angle 42, the suture guide 5 with needle pulling means is pulled back until its blunt distal end portion 14 is flush with the urethral stump 22 and the amount of bite 44 is controlled by the angle 42.

FIG. 9 and FIG. 10 illustrate a suture guiding device 46 of our invention in which the guide and shaft are integrally formed as one piece. This suture guiding device 46 comprises a shaft of circular cross section having a straight, long section 47 with a proximal end 58, a curved section 48, and a straight, short section 49 with a blunt end 50 formed with two slits 51 lying in planes extending endwise relative to shaft section 49 at a ninety degree angular orientation relative to one another, forming a cross shape at the distal end portion 57 of the guide. Each of these slits 51 has the same function as the slit 15 of the externally controlled, rotational suture guiding device 1. In this embodiment the sutures can be placed around the urethral stump only in four places oriented at ninety degrees relative to each other. Nevertheless it has the same advantage of the externally controlled, rotational suture guiding device 1, namely allowing the curved needle 20 to enter the urethral internal wall 30 near perpendicular, thereby causing the needle 20 to head in an exit direction the moment it starts to penetrate the urethral internal wall 30.

FIGS. 10A and 10B show two different possible orientations of the cross shape (made by the two slits 51) with respect to the straight long section 47.

FIG. 11 and FIG. 12 present another embodiment of the suture guiding device 46 shown in FIG. 9 and FIG. 10.

As shown in FIG. 11 and FIG. 12, the slit has side walls which converge distally outwardly away from the bottom surface of the slit, the slit 15 thus having a proximal portion with a wide separation 52 and a distal portion with a narrow separation 53 similar to the wide separation 33 and the narrow separation 34 of slit 15 of the externally controlled, rotational suture guiding device 1 described previously. This embodiment also incorporates the aforementioned needle pulling means.

Figure 13:
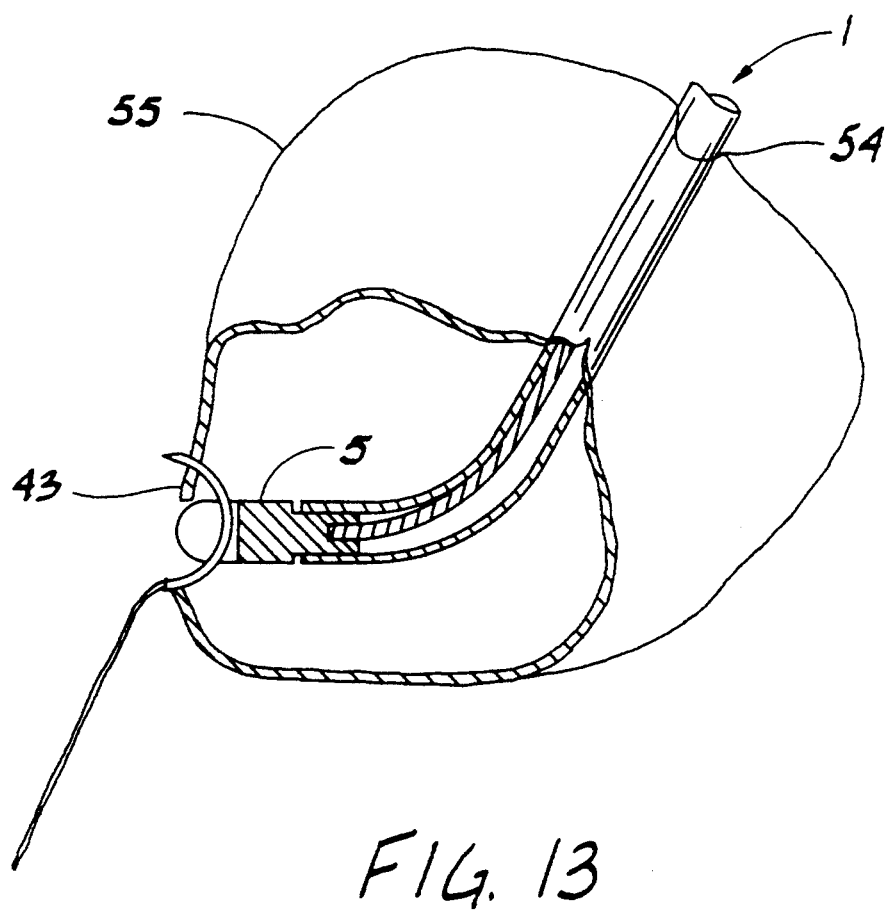
FIG. 13 illustrate a procedure for another usage of the device in FIG. 1, FIG. 9 and FIG. 11.

FIG. 13 presents another procedure for the usage of the externally controlled, rotational suture guiding device 1 incorporating a slit configured to pull a needle as described heretofore. In this procedure, the device is inserted through a cystotomy 54 in the bladder wall 55, allowing the suture guide 5 to exit through the bladder neck 43 during bladder reconstruction in order to assist the guiding of the suture to the bladder neck during anastomosis of the bladder to the urethra stump.

FIG. 14 and FIG. 15 present another instrument 59 of the present invention. As shown in FIG. 14, a suture guide 5 is provided at each end of the instrument creating a reversible, externally controlled, rotational suture guiding device with needle pulling means. This embodiment allows the surgeon to insert either end of this device first, giving the surgeon the choice between two different suture guides 5. For example, the slit(s) in one guide 5 may have parallel walls, and the slit in the other guide 5 may have converging side walls to provide the aforementioned needle pulling means.

FIG. 15 is a sectional view of a guide 5 shown in FIG. 14. This view illustrates how to assemble the instrument. Before assembling the instrument, the parts have to be made in a sequential order. One of the suture guides 5 is constructed with a hole 26 going through the entire length of the guide 5 but the slit 15 is not cut at this time. The other suture guide 5 is constructed with a partial hole 26 and with a slit 15. Then the tubular shaft 2 is bent to shape. To assemble the unit, join the suture guide 5 that has the slit, to the flexible shaft 4 in the same way that it is done for the instrument in FIG. 1 (bonded or brazed). The flexible shaft 4 is then inserted through the tubular shaft 2. Flexible shaft 4 is then inserted inside hole 26 of the other suture guide 5 (the one without a slit 15) and guide 5 is then slid up the flexible shaft 4 until suture guide 5 is inserted securely inside the short, straight tubular portion 6. By pulling flexible shaft 4 firmly while holding suture guide 5 (the one without the slit), the suture guide 5 at both ends of the suture guiding device 60 will be properly positioned inside respective ends 57 of the tubular shaft 2. Then the components of the suture guiding device 60 are held together by tightening set screw 61 against flexible shaft 4. After the instrument is an integral unit, a spot weld 62 at the head of the set screw 61 can be added and the excess ground smooth. This is done to prevent the set screw from backing up. Now it is possible to cut the slit 15 and to eliminate the excess of flexible shaft 4.

FIG. 16 presents another embodiment of the present invention. As it can be observed, suture guiding device 60 is of one piece construction and has suture guides 5 at both ends, like suture guiding device 46, thus creating a reversible device with needle pulling means. This embodiment also allows the surgeon to select either of two different suture guides, such as two guides having different diameters or slit configurations.

FIG. 17 presents another embodiment of the present invention. The instrument 63 in FIG. 17 is a flexible, externally controlled, rotational suture guiding device. This instrument 63 is similar to the externally controlled, rotational suture guiding device of FIG. 1, except it includes a flexible tubular shaft instead of a rigid tubular shaft. This instrument is comprised of a tubular shaft 64, having opposite ends which are distal 57 and proximal 58 relative to a person holding the device for use in a suturing procedure, the distal end 57 of the shaft being adapted to be inserted into a patient during the procedure. The device also includes a suture guide 5 mounted at the distal end 57 of the flexible tubular shaft 64 for rotation relative to the flexible tubular shaft 64 about an axis extending endwise with respect to the flexible tubular shaft 64, a control knob 3 at the proximal end 58 of the shaft and a flexible shaft 4 (not shown) inside the tubular shaft 64 interconnecting the suture guide portion 5 and the control knob 3. This instrument is especially suited for anastomosing two tubular structures during laparoscopic surgery.

This invention has been tested and found to be satisfactory for the accomplishment of the above objectives. While we have shown preferred embodiments thereof, we wish it to be specifically understood that our suture guiding device may take other forms without departing from the scope of our invention. For example, the control knob can be of different sizes and shapes, and it may have a narrow section spinning inside a tubular shaft with a large inside diameter at the control knob end.

It is also obvious that all sharp edges should be removed from the slit to protect the urethral internal wall.

It will also be understood that the configuration and number of slits in the suture guide 5 of our device may vary. For example, more than one or two slits may be provided, and the slits may be arranged at any angle relative to one another. The cross sectional shapes of a slit may also vary from the shapes shown in the drawings.

Our suture guides can be made of many kinds of materials. Stainless steel is best for reusable suture guides but for disposable suture guides, plastic, aluminum or a combination of both will do the job.

Having thus described our invention, what we claim is new and desire to secure by United States Letter Patent is:

1. A suture guiding device comprising a bent tubular shaft having opposite ends which are distal and proximal relative to a person holding the device for use in a suturing procedure, the distal end of the shaft being adapted to be inserted into a patient during said procedure, a suture guide mounted at the distal end of the shaft for rotation relative to the shaft about an axis extending endwise with respect to the shaft, said guide having a guide surface configured for guiding a curved suture needle in a desired direction as the needle is pushed along the surface, a hand-operable control device comprising a control knob rotatably mounted on said shaft generally adjacent its proximal end, and means interconnecting said guide and said control device comprising a flexible shaft inside said bent tubular shaft connected at one end to said control knob and at its other end to said guide whereby hand-operation of said control knob causes said flexible shaft and said guide to rotate to selectively adjust the suture-guiding position of said guide surface.

2. A suture guiding device comprising a tubular shaft having opposite ends which are distal and proximal relative to a person holding the device for use in a suture procedure, the distal end of the shaft being adapted to be inserted into a patient during said procedure, a suture guide mounted at the distal end of the shaft for rotation relative to the shaft about an axis extending endwise with respect to the shaft, said guide having a guide surface for guiding a suture needle, said guide extending endwise from the distal end of the shaft and having at least one end slit therein extending proximally inwardly from the distal end of the guide and laterally across the guide from one side of the guide to an opposite side of the guide, said end slit having a proximal portion adjacent the bottom of the slit forming a needle passage through the guide, from one side of the guide to said opposite side of the guide and a distal portion extending distally outwardly from the passage along the length of the passage, said needle passage having a surface, forming said guide surface, extending obliquely with respect to said axis of rotation and configured for guiding a suture needle pulling a suture thread as it passes through said passage, said suture thread being adapted to be removed from the guide after the suture needle has passed through said passage by moving the thread distally outwardly through the distal portion of the slit for exit from the slit, said suture guiding device further comprising a hand-operable control device mounted on the shaft generally adjacent its proximal end, and means interconnecting said guide and said control device whereby hand-operation of said control device effects rotation of the guide to selectively adjust the suture-guiding position of said guide surface.

3. A suture guiding device comprising a tubular shaft having opposite ends which are distal and proximal relative to a person holding the device for use in a suturing procedure, the distal end of the shaft being adapted to be inserted into a patient during said procedure, a suture guide mounted at the distal end of the shaft for rotation relative to the shaft about an axis extending endwise with respect to the shaft, said guide having a guide surface for guiding a suture needle, said guide extending endwise from the distal end of the shaft and having at least one end slit therein extending proximally inwardly from the distal end of the guide and laterally across the guide from one side of the guide to an opposite side of the guide, said end slit having a proximal portion adjacent the bottom of the slit forming a needle passage through the guide from one side of the guide to said opposite side of the guide, and a distal portion extending distally outwardly from the passage along the length of the passage, said needle passage having surface, forming said guide surface, configured for guiding a suture needle pulling a suture thread as it passes through said passage, in the distal portion of the end slit being narrower than said needle passage, said distal portion having a width sufficient to permit passage of a suture thread but insufficient to permit passage of a suture needle, the arrangement being such that, after the suture needle has passed through said needle passage, the suture thread is adapted to be removed from the guide by pulling the thread from the needle passage distally outwardly through the distal portion of the slit for exit from the slit, said suture guiding device further comprising a hand-operable control device mounted on the shaft generally adjacent its proximal end, and means interconnecting said guide and said control device whereby hand-operation of said control device effects rotation of the guide to selectively adjust the suture-guiding position of said guide surface.

4. A suture guiding device comprising a bent shaft having opposite ends which are distal and proximal relative to a person holding the device for use in a suturing procedure, said distal end of the shaft extending at an angle relative to a substantially straight section of the shaft and forming a suture guide adapted to be inserted into a patient during said procedure, and at least one outwardly opening, generally channel-shaped end slit in the guide extending endwise proximally inwardly from the distal end of the shaft and laterally across the shaft from one side of the shaft to an opposite side of the shaft, said end slit having a proximal portion adjacent the bottom of the slit forming a needle passage through the guide from one side of the guide to said opposite side of the guide, and a distal portion extending distally outwardly from the passage along the length of the passage to the distal end of the shaft, said end slit being open at its distal end to form a mouth at the distal end of the shaft, the bottom of the end slit forming a guide surface engageable by a suture needle and configured for guiding the needle as it is pushed along the guide surface in side-to-side direction with respect to the guide during said suturing procedure, said suture thread being adapted to be removed from the guide after the suture needle has passed through said passage by moving the thread from the proximal portion of the slit distally outwardly through the distal portion of the slit and through said open mouth of the slit at the distal end of the shaft for exit from the slit.

5. A suture guiding device comprising a tubular shaft having opposite ends which are distal and proximal relative to a person holding the device for use in a suturing procedure, the distal end of the shaft being adapted to be inserted into a patient during said procedure, a suture guide mounted at the distal end of the shaft for rotation relative to the shaft about an axis extending endwise with respect to the shaft, said guide having a guide surface for guiding a suture needle, said guide extending endwise from the distal end of the shaft and having more than one end slit in said guide, each end slit extending proximally inwardly from the distal end of the guide and laterally across the guide from one side of the guide to an opposite side of the guide, said slits lying in planes extending endwise of the guide at selected angular orientations relative to one another, each end slit having a proximal portion adjacent the bottom of the slit forming a needle passage through the guide from one side of the guide to said opposite side of the guide, and a distal portion extending distally outwardly from the passage along the length of the passage, each needle passage having a surface, forming said guide surface, configured for guiding a suture needle pulling a suture thread as it passes through said passage, said suture guiding device further comprising a hand-operable control device mounted on the shaft generally adjacent its proximal end, and means interconnecting said guide and said control device whereby hand-operation of said control device effects rotation of the guide to selectively adjust the suture-guiding position of said guide surface.

6. A suture guiding device as set forth in claim 5 wherein there are two end slits disposed generally at right angles relative to one another, said slits generally along a line coincident with said axis of rotation of the guide.

7. A suture guiding device comprising a tubular shaft having opposite ends which are distal and proximal relative to a person holding the device for use in a suturing procedure, said shaft having a generally straight distal end section, a generally straight proximal end section, and a middle section extending between the two end sections, said distal and proximal end sections extending from said middle section at oblique angles with respect thereto, the distal end of the shaft being adapted to be inserted into a patient during said procedure, the suture guiding device further comprising a suture. guide mounted at the distal end of the shaft for rotation relative to the shaft about an axis extending endwise with respect to the shaft, said guide having a guide surface for guiding a suture needle, a hand-operable control device mounted on the shaft generally adjacent its proximal end, and means interconnecting said guide and said control device whereby hand-operation of said control device effects rotation of the guide to selectively adjust the suture-guiding position of said guide surface.

8. A suture guiding device as set forth in claim 7 wherein the longitudinal axes of said distal and proximal sections of the shaft are generally parallel to one another.

9. A suture guiding device comprising a shaft having opposite ends which are distal and proximal relative to a person holding the device for use in a suturing procedure, said distal end of the shaft forming a suture guide and being adapted to be inserted into a patient during said procedure, and at least one outwardly opening, generally channel-shaped end slit in the guide extending endwise proximally inwardly from the distal end of the shaft and laterally across the shaft from one side of the shaft to an opposite side of the shaft, said end slit having a proximal portion adjacent the bottom of the slit forming a needle passage through the guide from one side of the guide to said opposite side of the guide, and a distal portion extending distally outwardly from the passage along the length of the passage to the distal end of the shaft, said end slit being open at its distal end to form a mouth at the distal end of the shaft, said needle passage having a guide surface configured for guiding a suture needle pulling a suture thread as it passes through said passage, said suture thread being adapted to be removed from the guide after the suture needle has passed through said passage by moving the thread from the proximal portion of the slit distally outwardly through the distal portion of the slit and through said open mouth of the slit at the distal end of the shaft for exit from the slit.

10. A suture guiding device as set forth in claim 9 wherein said guide surface extends generally at right angles to the longitudinal axis of the shaft at its distal end.

11. A suture guiding device as set forth in claim 9 wherein said shaft is flexible.

12. A suture guiding device comprising a shaft having opposite ends which are distal and proximal relative to a person holding the device for use in a suturing procedure, said distal end of the shaft forming suture guide and being adapted to be inserted into a patient during said procedure, and at least one end slit in the guide extending endwise proximally inwardly from the distal end of the shaft and laterally across the shaft from one side of the shaft to an opposite side of the shaft, said end slit having a proximal portion adjacent the bottom of the slit forming a needle passage through the guide from one side of the guide to said opposite side of the guide, and a distal portion extending distally outwardly from the passage along the length of the passage, said needle passage having a guide surface extending obliquely with respect to the longitudinal axis of the shaft at its distal end and configured for guiding a suture needle pulling a suture thread as it passes through said passage, said suture thread being adapted to be removed from the guide after the suture needle has passed through said passage by moving the thread from the proximal portion of the slit distally outwardly through the distal portion of the slit and through said open mouth of the slit at the distal end of the shaft for exit from the slit.

13. A suture guiding device comprising a shaft having opposite ends which are distal and proximal relative to a person holding the device for use in a suturing procedure, said distal end of the shaft forming a suture guide and being adapted to be inserted into a patient during said procedure, and at least one end slit in the guide extending endwise proximally inwardly from the distal end of the shaft and laterally across the shaft from one side of the shaft to an opposite side of the shaft, said end slit having a proximal portion adjacent the bottom of the slit forming a needle passage through the guide from one side of the guide to said opposite side of the guide, and a distal portion extending distally outwardly from the passage along the length of the passage, said needle passage having a guide surface configured for guiding a suture needle pulling a suture thread as it passes through said passage, the distal portion of the end slit being narrower than said needle passage, said distal portion having a width sufficient to permit passage of a suture thread but insufficient to permit passage of a suture needle, the arrangement being such that, after the suture needle has passed through said needle passage, the suture thread is adapted to be removed from the guide by pulling the thread from the needle passage distally outwardly through the distal portion of the slit for exit from the slit.

14. A suture guiding device as set forth in claim 13 wherein said distal and proximal portions of the end slit have side walls converging toward one another in a direction away from the bottom of the slit.

15. A suture guiding device comprising a shaft having opposite ends which are distal and proximal relative to a person holding the device for use in a suturing procedure, said distal end of the shaft forming a suture guide and being adapted to be inserted into a patient during said procedure, and at least two end slits in the guide extending endwise proximal inwardly from the distal end of the shaft and laterally across the shaft from one side of the shaft to an opposite side of the shaft, said slits lying in planes extending endwise of the shaft at selected angular orientations relative to one another, each of said end slits having a proximal portion adjacent the bottom of the slit forming a needle passage through the guide from one side of the guide to said opposite side of the guide, and a distal portion extending distally outwardly from the passage along the length of the passage, said needle passage having a guide surface configured for guiding a suture needle pulling a suture thread as it passes through said passage, said suture thread being adapted to be removed from the guide after the suture needle has passed through said passage by moving the thread from the proximal portion of the slit distally outwardly through the distal portion of the slit and through said open mouth of the slit at the distal end of the shaft for exit from the slit.

16. A suture guiding device comprising a shaft having opposite ends which are distal and proximal relative to a person holding the device for use in a suturing procedure, said distal end of the shaft forming a suture guide and being adapted to be inserted into a patient during said procedure, and two end slits extending endwise proximally inwardly from the distal end of the shaft and laterally across the shaft from one side of the shaft to an opposite side of the shaft, said end slits lying in planes extending endwise of the guide and disposed generally at right angles relative to one another, said end slits intersecting generally along a line coincident with the longitudinal axis of the shaft at its distal end, each end slit having a proximal portion adjacent the bottom of the slit forming a needle passage through the guide from one side of the guide to said opposite side of the guide, and a distal portion extending distally outwardly from the passage along the length of the passage, said needle passage having a guide surface configured for guiding a suture needle pulling a suture thread as it passes through said passage.

17. A suture guiding device comprising a shaft having opposite ends which are distal and proximal relative to a person holding the device for use in a suturing procedure, each of said opposite ends of the shaft forming a suture guide adapted to be inserted into a patient during said procedure and at least one end slit in each guide extending endwise proximally inwardly from the distal end of the shaft and laterally across the shaft from one side of the shaft to an opposite side of the shaft, each end slit having a proximal portion adjacent the bottom of the slit forming a needle passage through the guide from one side of the guide to said opposite side of the guide and a distal portion extending distally outwardly from the passage along the length of the passage, each needle passage having a guide surface configured for guiding a suture needle pulling a suture thread as it passes through said passage, said suture thread being adapted to be removed from each guide after the suture needle has passed through said passage by moving the thread from the proximal portion of the slit distally outwardly through the distal portion of the slit for exit from the slit.

18. A suture guiding device as set forth in claim 17 wherein the distal end of the shaft is configured different from the suture guide at the proximal end of the shaft whereby a person using the device may choose between said two guides according to the suturing procedure to be carried out.

19. A suture guiding device as set forth in claim 18 wherein said slit in one of said two guides has parallel side walls and said slit of the other of said two guides has converging side walls providing needle pulling means.

20. A method of performing a suturing procedure on an anatomical element utilizing a suture guiding device of the type comprising a shaft having opposite ends which are distal and proximal relative to a person holding the device for use in said suturing procedure, a guide at the distal end of the shaft, and at least one end slit in the guide extending proximally inwardly from a distal end of the guide and laterally across the guide from one side of the guide to an opposite side of the guide, said slit having a proximate portion adjacent the bottom of the slit forming a needle passage, and a distal portion extending distally outwardly from the needle passage along the length of the passage, said passage having a guide surface, said method comprising the steps of:
  inserting the shaft into a patient to a preliminary position in which the guide projects distally beyond said element to be sutured;
  placing at least the tip of a suture needle in said end slit in the guide so that the tip is unexposed to said element; retracting the shaft and the guide with at least the tip of the needle therein to a suturing position in which the needle is positioned for suturing said element;
  passing the suture needle through said needle passage in the guide with the needle in contact with said guide surface so that the needle is guided into and through said element to be sutured for a distance sufficient to pull a leading length of suture thread through the element while leaving a trailing length of suture thread in the guide; and
  removing the trailing length of thread from the guide by passing it distally outwardly through the outwardly opening distal portion of the slit.

21. A method as set forth in claim 20 wherein said suturing procedure is a radical prostatectomy for suturing together the severed end of the urethral tube and a bladder neck, and wherein the method involves insertion of the shaft of the suture guiding device through the urethral tube to a position in which the guide projects distally beyond the severed end of the tube and surrounding tissue, placing at least the tip of the suture needle in the slit, and retracting the shaft to position the guide inside the urethral tube so that the needle may be guided through a wall of the tube.

22. A method as set forth in claim 20 wherein the distal portion of the end slit is narrower than said needle passage, the distal portion having a width sufficient to permit passage of suture thread but insufficient to permit passage of a suture needle, said method further comprising:
  lodging a tapered tip of the suture needle in said distal portion of the slit prior to retraction of the shaft so that the needle is held by the guide as the shaft is retracted to its said suturing position;
  dislodging the tapered tip of the suture needle from the distal portion of the slit; and moving the needle through said needle passage while in contact with said guide surface.

* * * * *